(12) United States Patent
Helmig et al.

(10) Patent No.: US 6,350,056 B1
(45) Date of Patent: Feb. 26, 2002

(54) METHOD FOR FIBER OPTIC TEMPERATURE MEASUREMENT AND FIBER OPTIC TEMPERATURE SENSOR

(75) Inventors: Christian Helmig, Werl; Jörg Teunissen, Ratingen, both of (DE)

(73) Assignee: Maschinenfabrik Reinhausen GmbH, Regensburg (DE)

( * ) Notice: Subject to any disclaimer, the term of this patent is extended or adjusted under 35 U.S.C. 154(b) by 29 days.

(21) Appl. No.: 09/652,102

(22) Filed: Aug. 30, 2000

(30) Foreign Application Priority Data

Sep. 2, 1999 (DE) ........................... 199 41 832

(51) Int. Cl.[7] ........................ G01K 11/32; G02B 6/00
(52) U.S. Cl. ..................... 374/161; 374/120; 385/12
(58) Field of Search ............................. 374/161, 120; 385/12

(56) References Cited

U.S. PATENT DOCUMENTS

| | | | | |
|---|---|---|---|---|
| 4,201,446 A | * | 5/1980 | Geddes et al. | 350/96.29 |
| 4,461,574 A | * | 7/1984 | Shaw et al. | 356/350 |
| 4,659,923 A | * | 4/1987 | Hicks, Jr. | 250/227 |
| 4,729,622 A | * | 3/1988 | Pavlath | 350/96.15 |
| RE33,064 E | * | 9/1989 | Carter et al. | 436/34 |
| 4,904,085 A | * | 2/1990 | Spillman, Jr. et al. | 356/364 |
| 5,007,705 A | * | 4/1991 | Morey et al. | 350/96.29 |
| 5,448,657 A | * | 9/1995 | Kim et al. | 385/12 |
| 5,483,607 A | * | 1/1996 | O'Keefe | 385/11 |
| 6,188,812 B1 | * | 2/2001 | Kao et al. | 385/12 |
| 6,304,686 B1 | * | 10/2001 | Yamate et al. | 385/13 |

FOREIGN PATENT DOCUMENTS

| | | |
|---|---|---|
| DE | 2936303 | 4/1981 |
| DE | 19644 885 A1 | 4/1998 |
| GB | 2197067 | 5/1988 |

OTHER PUBLICATIONS

Hadeler et al., "Polarimetric distributed feedback fiber laser sensor for simultanious strain and temperature measurements", Journal of Electronics Letters, Nov. 25, 1982, vol. 18, No. 24, pp. 1022–1023.

D. Langeae, "Temperature sensing in twisted single–mode fibers", Journal of Applied Optics, Apr. 1, 1999, vol. 38, No. 10, pp. 1953–1957.

"Polarimetric Distributed Feedback Fiber Lase Sensor for Simultaneous. . . ", Oliver Hadeler et al; Apr. 1, 1999, vol. 38, No. 10//Applied Optics; 6 pages.

* cited by examiner

*Primary Examiner*—Diego Gutierrez
*Assistant Examiner*—Lydia M. De Jesús
(74) *Attorney, Agent, or Firm*—Herbert Dubno

(57) ABSTRACT

Fiber optic temperature measurement, especially for electric power equipment is effected utilizing, as the sensor, a portion of an optical fiber from which the coating has been removed and to which a glass capillary has been bonded by an adhesive. The measurement is carried out polarimetrically and utilizes the change in birefrigence resulting from a temperature change because of the mechanical stressing of the sensor region of the optical fiber.

14 Claims, 3 Drawing Sheets

METHOD FOR FIBER OPTIC TEMPERATURE MEASUREMENT AND FIBER OPTIC TEMPERATURE SENSOR

FIELD OF THE INVENTION

Our present invention relates to a method of fiber optic temperature measurement and a fiber optic temperature sensor suitable for the online monitoring of the temperatures of electrical components and apparatus, especially electrical units utilized in the generation and distribution of electrical energy.

BACKGROUND OF THE INVENTION

For online monitoring of units utilized in the production and distribution of electrical energy, for safety and reliability it is important to determine the temperature at critical portions of the apparatus or device or at critical components thereof. For this purpose, a potential free temperature measurement is required and, increasingly, fiber optic measuring systems have been involved in such monitoring.

Fiber grating sensor systems are known for temperature measurement and are potentially suitable for monitoring the temperatures of such equipment. Thus, for the sensitization of standard quartz glass fibers temperature measurement, microstructured refraction gratings can be "written" in the core of the light waveguide at defined locations along the glass fiber. These gratings which are monolithically formed in the fiber, for example so called Bragg gratings, are capable of reflecting certain wavelengths of the light. The reflection wavelength is dependent, inter alia upon fiber temperature. The fiber grating sensor systems, however, have the disadvantage that the "writing" of the grating requires a relatively expensive scanning method or the application of short laser pulses during the glass fiber drawing process which is also expensive.

Point sensitive systems utilizing fiber optics are also known and operate in accordance with various principles: Luminescence temperature sensors based upon the known characteristics of photoluminescence of various materials utilize the fact that the materials can be excited to emit characteristic longer wave radiation at certain spectral ranges by comparison to the excitation light. The measured parameter can thus either be the temperature-dependent change in the spectral intensity distribution or the extinction time of the luminescence.

Thermochromic temperature sensors utilize the effect that amplitude and the spectral location of light absorption is temperature dependent in solid and liquid substances. The strength of the absorption or transmission is thus a measure of the detected temperature.

Interferometric temperature sensors utilize the effect of temperature on the phase. They are highly temperature sensitive but generally the sensor region cannot be localized with sufficient precision.

Polarimetric sensors utilize the temperature dependence of birefrigence upon the phase of the lightwave. The temperature sensitivity is especially great with strongly birefringent fibers and as a consequence commercially HIBI fibers (high birefringent) are used. Such a polarimetric sensor is described in DE 196 44 85 A1, by way of example. A drawback with such sensors is that even the feed portions of the fiber leading to the sensor region are temperature sensitive and thus it is not possible to obtain point-wise temperature detection at specific locations of an electrical unit as is required.

OBJECTS OF THE INVENTION

It is, therefore, an object of the invention to provide a polarimetric fiber optic fiber optic temperature measurement process and a fiber optic temperature sensor for such a polarimetric process, whereby the sensor is of simple construction and easy to operate, permits spatially defined temperature measurements to be made with precision, and enables standard components to be utilized with the temperature sensor.

Another object of the invention is to provide a method of measuring temperature which is particularly suitable for use in the monitoring of the temperature of electrical apparatus and devices, especially for use in the production an distribution of electrical energy.

It is also an object of this invention to provide an improved temperature sensor which allows highly localized and pressure temperature arrangements to be made without the drawbacks of earlier systems.

SUMMARY OF THE INVENTION

These objects and others which will become apparent hereinafter are attained, in accordance with the invention in a method of measuring temperature, especially at apparatus or equipment for the production and distribution of electrical energy which comprises the steps of:

(a) providing a polarimetrically effective fiber-optic glass fiber with a temperature-measurement region in which a coating has been removed from an optical fiber core and the core in this region is cemented to a glass capillary by a hardened adhesive;

(b) coupling into an end of the fiber-optic glass fiber on one side of the region light of a certain polarization state whereby polarization of the light is altered as a function of the temperature in the region; and (c) measuring a difference in polarization of the light in the fiber on an opposite side of the region from the certain polarization state and thereby calculating a temperature in the region from the difference.

The temperature calculated in step (c) can be a temperature difference over time or the absolute temperature, i.e. a temperature of a region or a temperature differential. The difference in polarization is preferably measured by a polarimeter and the light can be coupled into the aforementioned end of the fiber optic glass fiber through a polarizer.

The fiber optic temperature sensor can comprise:

a polarimetrically effective fiber-optic glass fiber with a temperature-measurement region in which a coating has been removed from an optical fiber core and the core in this region is cemented to a glass capillary by a hardened adhesive;

means for coupling into an end of the fiber-optic glass fiber on one side of the region light of a certain polarization state whereby polarization of the light is altered as a function of the temperature in the region; and means for measuring a difference in polarization of the light in the fiber on an opposite side of the region from the certain polarization state and thereby calculating a temperature in the region from the difference.

The temperature sensor can be a glass fiber especially sensitive to mechanical pressure and, for example, a Lo-Bi (low birefrigence) fiber.

Preferably the adhesive is an epoxy resin adhesive with a thermal coefficient of expansion of about $90 \times 10^{-6} K^{-1}$. The preferred adhesive is a Delo™ adhesive.

The glass capillary can be composed of quartz glass with a coefficient of thermal expansion of $0.5 \times 10^{-6} K^{-1}$.

With the invention, the temperature dependent birefringence effect is confined to a precisely defined narrow region of the glass fiber, namely that region in which the glass fiber, from which the coating has been removed, is bonded by the adhesive to the glass capillary. This region serves to produce a measured temperature value for the potential-free detection of the temperature in apparatus, devices and units utilized in the production and distribution of electrical energy, such as power transformers and/or electrical power switches and tapping units for such power transformers.

The sensor is particularly advantageous since it allows precise determination of the region at which the temperature is detected which is particularly important for such monitoring. It is only the region of the glass fiber which is surrounded by the glass capillary and at which the space between the fiber and the glass capillary is bridged by the sensor that functions as the temperature detector. This region, which can have the length of say a centimeter, allows measurement of temperature changes with high precision because of the significant changes in the polarization of the glass fiber in this region.

BRIEF DESCRIPTION OF THE DRAWING

The above and other objects, features, and advantages will become more readily apparent from the following description, reference being made to the accompanying drawing in which:

FIG. 2A is a detail of the region IIA of FIG. 2; and

SPECIFIC DESCRIPTION

Figure 1:
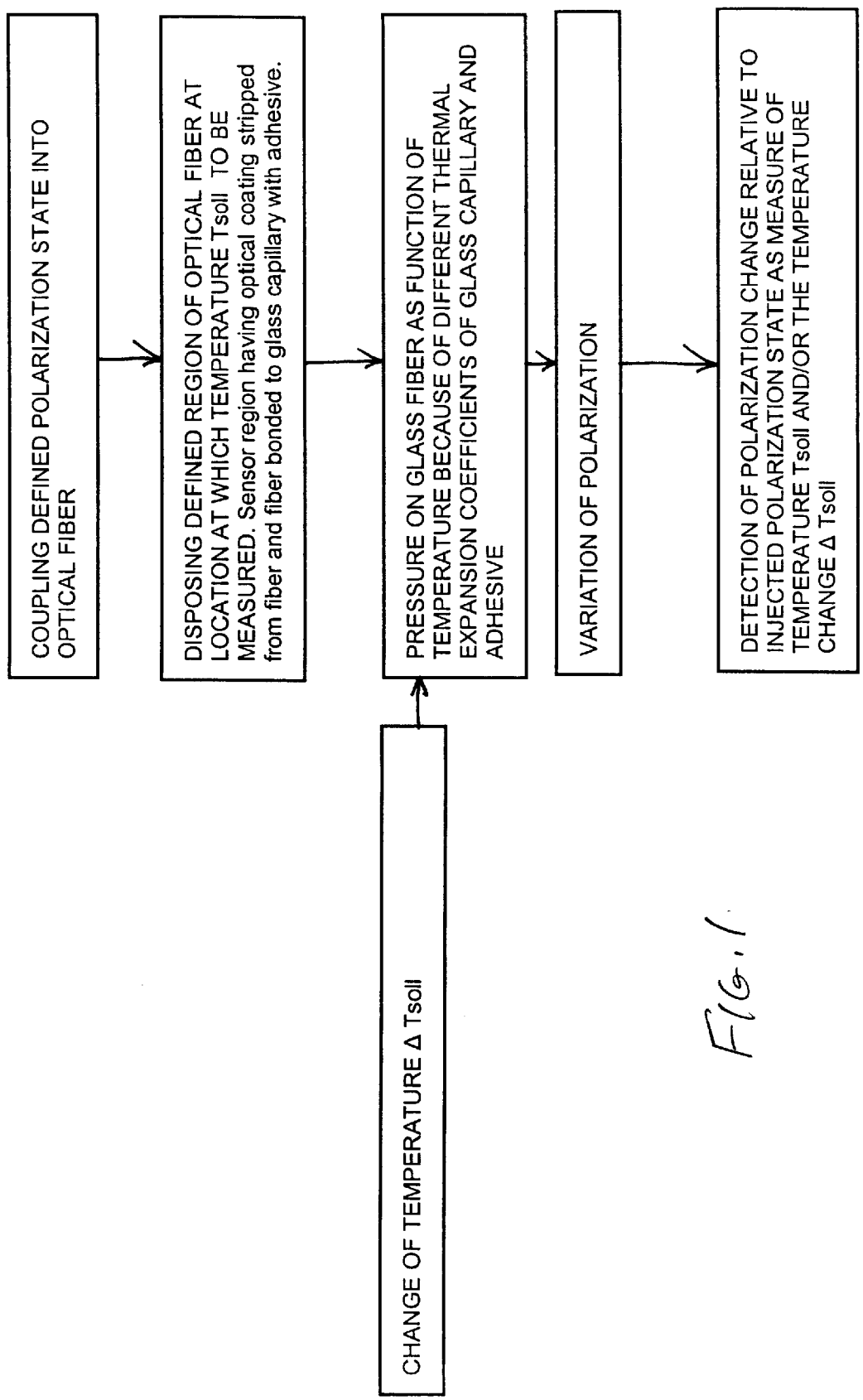
FIG. 1 is a flow diagram illustrating the method of the invention.

In FIG. 1 we have provided an information flow diagram of the process for fiber optic temperature measurement. As can be seen from this sequence, a polarization state is initially coupled into the glass fiber which has its sensor region in the region of the temperature measurement to be effected. This coupling of a defined polarization state from a region outside the apparatus or device to be monitored can be effected by a laser which can be connected to the optical fiber through an adjustable polarizer. The glass fiber has in the region at which the temperature is to be measured, a portion of the fiber from which the outer sheath or coating has been removed, e.g. of a length in the millimeter or centimeter range and surrounded by a glass capillary which need not be longer than the uncoated region or, if longer, is not substantially longer. The glass capillary surrounds the uncoated region of the fiber with a clearance which is filled with an adhesive.

The laser and polarizer are provided at one end of this glass fiber and at the opposite end a polarimeter is provided which can detect the polarization change.

Because of the different thermal coefficients of expansion of glass on the one hand and the adhesive on the other, temperature changes in the glass fiber surrounded by the capillary give rise to a mechanical pressure which affects the polarization in the glass fiber. This polarization change is a measure of the instantaneous temperature in the apparatus at the point at which the capillary surrounds the glass fiber and is detected by the polarization. The change in polarization provides a measurement of the absolute temperature $T_{soll}$ or a temperature change $\Delta T_{soll}$.

Figure 2:
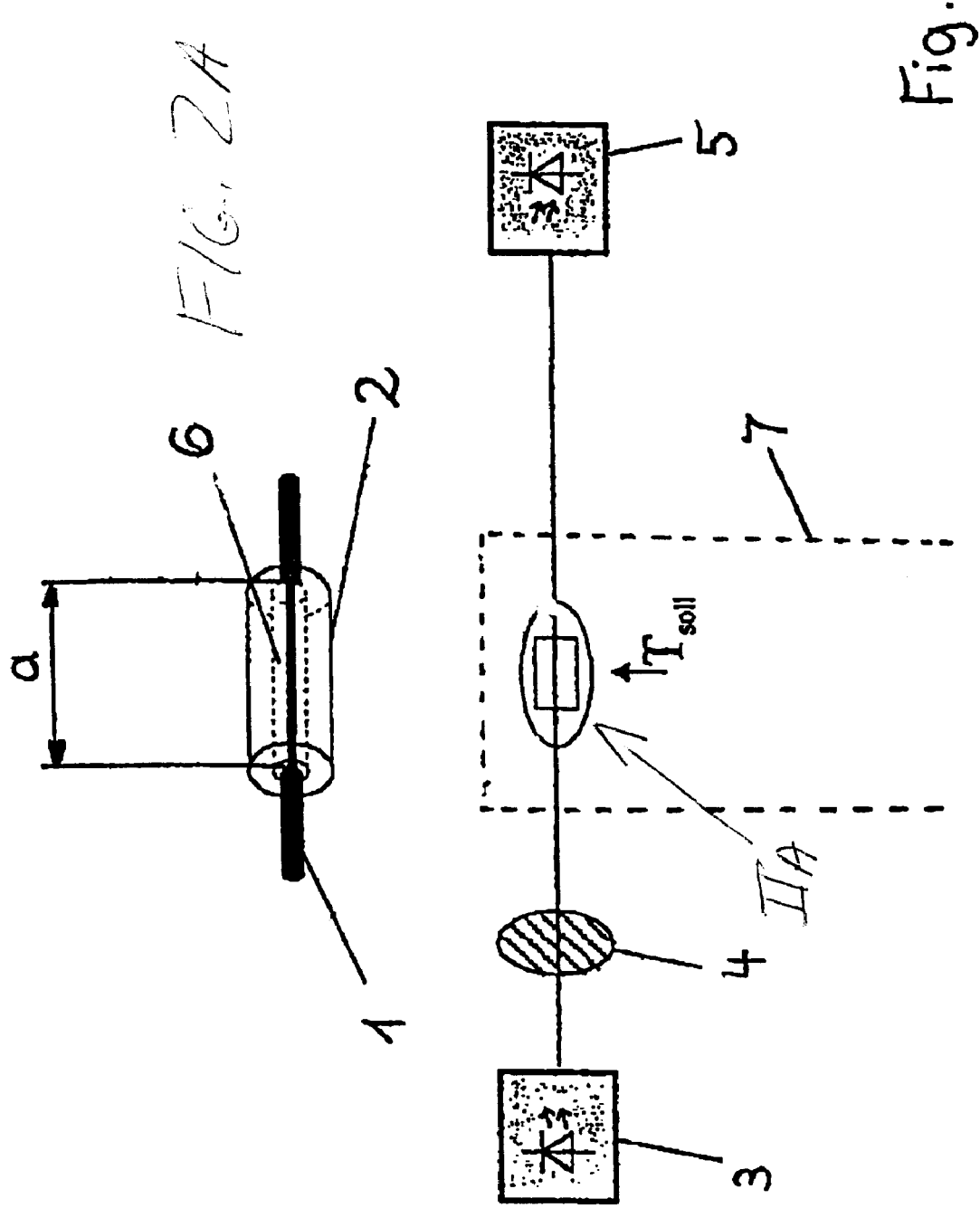
FIG. 2 is a diagram of the apparatus of the invention.

FIGS. 2 and 2A show the fiber optic temperature sensor system and constitutes a low cost sensor for the temperature in, for example, a power transformer 7.

In these figures the glass fiber 1 is shown to be stripped over a given portion (a) of its length and in the region exposed to the ambient temperature $T_{soll}$ from its coating, surrounded by the glass capillary 2 and bonded to the glass capillary 2 by an adhesive 6. The temperature $T_{soll}$ is measured within the transformer at an appropriate location. The transformer 7 has been shown only schematically by broken lines. The glass capillary 2 has an internal diameter which is larger than the external diameter of the glass fiber in the region which the coating is stripped therefrom. At one end of the glass fiber 1 a laser 3 injects a light beam into the fiber through a polarizer 4 and at the opposite end of the glass fiber a polarimeter is provided to read out the change in polarization directly as a temperature change or as the absolute temperature. The glass fiber 1 is advantageously a LoBi-fiber which is especially sensitive to mechanical pressure. The adhesive 6 is for example an epoxy resin adhesive of the type marketed as Delo with a coefficient of thermal expansion of $90 \times 10^{-6} K^{-1}$. The glass capillary 2 is composed of quartz glass with a coefficient of thermal expansion of $0.5 \times 10^{-6} K^{-1}$. When the temperature $T_{soll}$ in the sensor region varies, a mechanical pressure develops in the sensor region of the glass fiber which changes the polarization to allow this temperature change to be registered at the polarimeter 5.

Figure 3:
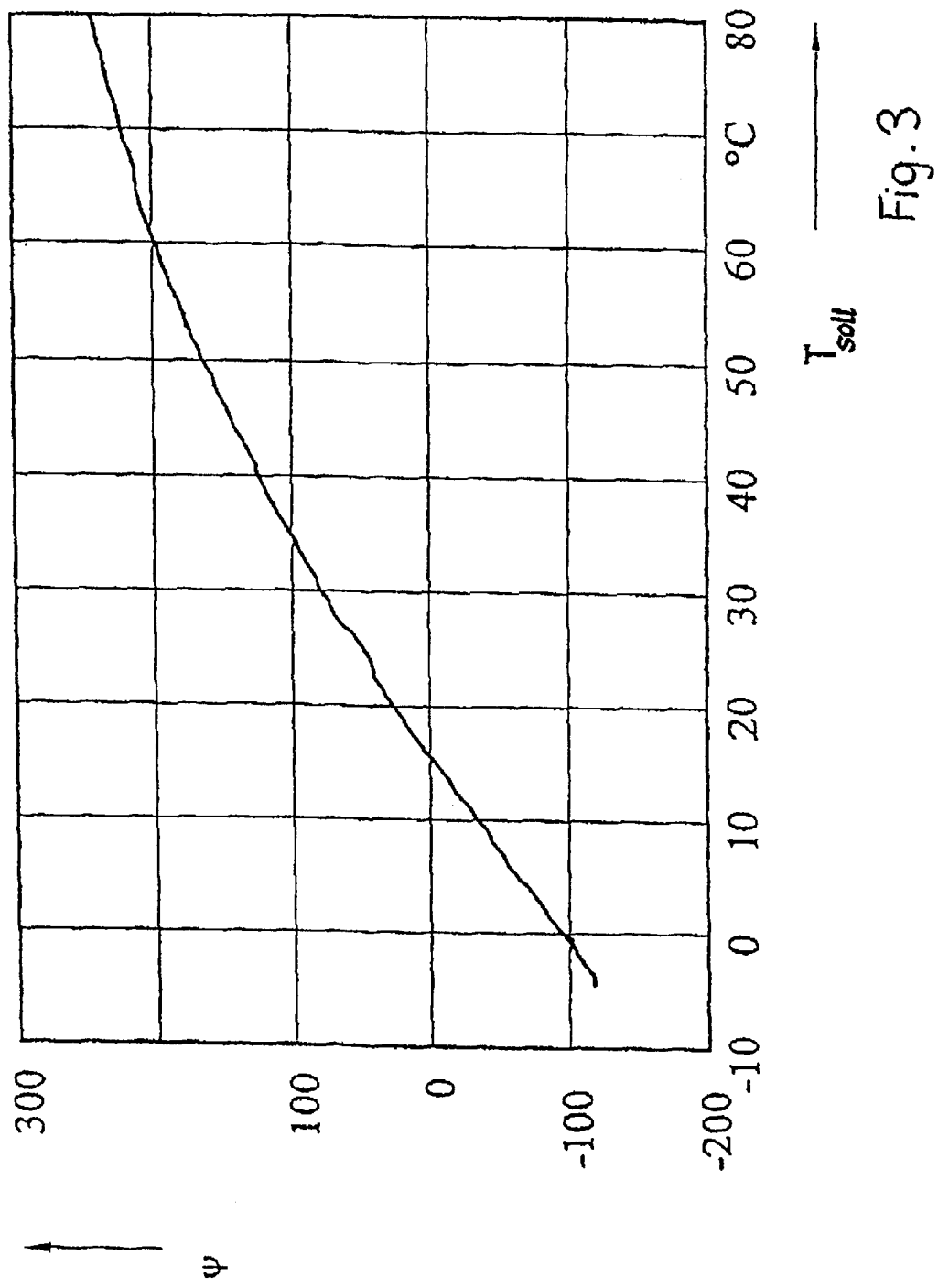
FIG. 3 is a graph of the birefrigence as a function of the temperature.

FIG. 3 shows the effect of the linear birefrigence according to the invention characterized by the ellipticity angle $\psi$ over a wide temperature range $T_{soll}$ this parameter varies monotonically and this change in the ellipticity of the lightwave is detected by the polarimeter 5. The illustrated relationship has been provided utilizing the commercial adhesive Delo-Katiobond 4594. It is also possible in a so-called all fiber construction with a suitable orientation of an analyzer to convert this ellipticity to a direct intensity measurement. The birefrigence varies as a function of the mechanical distortion and there is a cosine relationship between the polarization angle and the intensity as measured at the analyzer. Any undesired ambiguity in the signal can, however, be eliminated by a matching of the region (a) of the fiber from which the coating has been removed.

The result is a low coat potential free temperature sensor which is highly suitable for monitoring the temperature of an electrical unit of the type described at precise points.

We claim:

1. A method of measuring temperature comprising the steps of:
   (a) providing a polarimetrically effective fiber-optic glass fiber with a temperature-measurement region in which a coating has been removed from an optical fiber core and the core in this region is cemented to a glass capillary by a hardened adhesive;
   (b) coupling into an end of said fiber-optic glass fiber on one side of said region light of a certain polarization state whereby polarization of the light is altered as a function of the temperature in said region; and
   (c) measuring a difference in polarization of the light in said fiber on an opposite side of said region from said certain polarization state and thereby calculating a temperature in said region from said difference.

2. The method defined in claim 1 wherein said temperature calculated in step (c) is a temperature of said region.

3. The method defined in claim 1 wherein said temperature calculated in step (c) is a temperature difference over time.

4. The method defined in claim 1 wherein said difference in polarization is measured in step (c) by a polarimeter.

5. The method defined in claim 1 wherein the light is coupled into said end of said fiber-optic glass fiber through a polarizer.

6. A fiber-optic temperature sensing apparatus comprising:

a polarimetrically effective fiber-optic glass fiber with a temperature-measurement region in which a coating has been removed from an optical fiber core and the core in this region is cemented to a glass capillary by a hardened adhesive;

means for coupling into an end of said fiber-optic glass fiber on one side of said region light of a certain polarization state whereby polarization of the light is altered as a function of the temperature in said region; and means for measuring a difference in polarization of the light in said fiber on an opposite side of said region from said certain polarization state and thereby calculating a temperature in said region from said difference.

7. The apparatus defined in claim 6 wherein said fiber is a LoBi glass fiber sensitive to mechanical pressure.

8. The apparatus defined in claim 6 wherein said adhesive is an epoxy resin adhesive with a thermal coefficient of expansion of about $90 \times 10^{-6} K^{-1}$.

9. The apparatus defined in claim 8 wherein said adhesive is a Delo-adhesive.

10. The apparatus defined in claim 8 wherein said glass capillary is composed of quartz glass with a coefficient of thermal expansion of $0.5 \times 10^{-6} K^{-1}$.

11. The apparatus defined in claim 10 wherein the calculated temperature is a temperature of said region.

12. The apparatus defined in claim 10 wherein said calculated temperature is a temperature difference over time.

13. The apparatus defined in claim 10 wherein said means for measuring said difference in polarization is a polarimeter.

14. The apparatus defined in claim 10 wherein said means for coupling the light into said end of said fiber-optic glass fiber is a polarizer.

* * * * *